United States Patent [19]
Challis et al.

[11] Patent Number: 5,807,542
[45] Date of Patent: Sep. 15, 1998

[54] CHEMICAL COMPOSITIONS FOR INHIBITING NITROSATION REACTION IN TOILETRIES AND COSMETICS

[75] Inventors: Brian Christopher Challis, Milton Keynes; Walter Graham Guthrie; David Vincent Roper, both of Nottingham; David Frank Trew, Milton Keynes, all of Great Britain

[73] Assignee: Knoll Aktiengesellschaft, Ludwigshafen, Germany

[21] Appl. No.: 649,587

[22] PCT Filed: Oct. 3, 1994

[86] PCT No.: PCT/EP94/03264

§ 371 Date: May 28, 1996

§ 102(e) Date: May 28, 1996

[87] PCT Pub. No.: WO95/14457

PCT Pub. Date: Jun. 1, 1995

[30] Foreign Application Priority Data

Nov. 27, 1993 [GB] United Kingdom .................. 9324426
Jul. 23, 1994 [GB] United Kingdom .................. 9414886

[51] Int. Cl.⁶ .............................. A61K 7/42; A61K 7/15; A61K 31/04
[52] U.S. Cl. .............................. 424/59; 424/73; 514/846; 514/847; 514/848
[58] Field of Search ................. 424/73, 59; 514/846, 514/847, 848

[56] References Cited

U.S. PATENT DOCUMENTS

| | | | |
|---|---|---|---|
| 4,189,465 | 2/1980 | Rosenthal | 424/10 |
| 4,200,542 | 4/1980 | Sedlak | 252/25 |
| 4,251,563 | 2/1981 | Gruetzmacher et al. | 426/605 |
| 4,331,468 | 5/1982 | Williams | 504/326 |
| 4,342,789 | 8/1982 | Ueno et al. | 426/266 |
| 4,368,330 | 1/1983 | Andrews | 549/315 |
| 4,443,483 | 4/1984 | Sato et al. | 426/266 |
| 4,576,825 | 3/1986 | Tracy et al. | 426/266 |

FOREIGN PATENT DOCUMENTS

| | | |
|---|---|---|
| 024 114 | 2/1981 | European Pat. Off. . |
| 031 284 | 7/1981 | European Pat. Off. . |
| 058 492 | 8/1982 | European Pat. Off. . |
| 112 100 | 6/1984 | European Pat. Off. . |
| 344 564 | 12/1989 | European Pat. Off. . |
| 445 924 | 9/1991 | European Pat. Off. . |
| 498 346 | 8/1992 | European Pat. Off. . |
| 553 800 | 8/1993 | European Pat. Off. . |
| 22 74 648 | 8/1994 | United Kingdom . |
| 92/00122 | 1/1992 | WIPO . |
| 92/19951 | 11/1992 | WIPO . |
| 93/11742 | 6/1993 | WIPO . |
| 93/22273 | 11/1993 | WIPO . |

OTHER PUBLICATIONS

Derwent Abstracts, AN 93–079423 [10] (English abstract of JP 910204860, Jul. 20. 1991).
Derwent Abstracts, AN 91–350854 [48] (English abstract of JP 900029818, Feb. 9, 1990).
Fellion et al., IARC Science Publication No. 31, 1980, pp. 435–443.
Kabacoff et al., IARC Science Publication No. 57, 1984, pp. 347–352.
Kabacoff et al., JACS Symposium Series, No. 174, 1981 part 174, pp. 149–156.
Dunnett et al., *Int'l. J. of Cosmetic Science*, vol. 6, pp. 241–247, 1984.
Havery et al., *ACS Symp. Series 553* Chap. 2, pp. 20–33, 1994.
Casado et al., *J. Chem. Soc. Perkin Trans. II*, pp. 1963–1966, 1984.
Wilcox et al., *Chem. Res. Toxicol.*, vol. 4, pp. 373–381, 1991.
Schmeltz et al., *Fd. Cosmet. Toxicol.*, vol. 17, pp. 105–109, 1979.
*Chem. Abst.*, vol. 115, 182618f, 1991 (DE 3,939,475).
Kirk–Othmer, *Enc. of Chem. Tech.*, 3rd Ed., vol. 15, pp. 988–996.
Ikeda et al., *J. Soc. Cosmet. Chem.*, vol. 41, pp. 283–333, Sep./Oct. 1990.
Ong et al., *J. Soc. Cosmet. Chem.*, vol. 31, pp. 153–159, May/Jun. 1980.
Bharucha et al., *J. Argic. Food Chem.*, vol. 35, pp. 915–917, 1987.
Bao et al., *Chem. Res. Toxicol.*, vol. 4, pp. 382–389, 1991.
Keefer et al., *Science*, vol. 181, pp. 1245–1247, Sep. 1973.
Rosenberg et al., *CFTA Cosmetic Journal*, pp. 30–37, 1981.

*Primary Examiner*—Alan Rotman
*Attorney, Agent, or Firm*—Keil & Weinkauf

[57] ABSTRACT

Iminium ion scavengers are used in the invention to inhibit formation of N-nitrosamines, especially in cosmetics and pharmaceuticals formulations. The iminium ion scavengers may be used in combination with nitrite ion scavengers such as ascorbate.

12 Claims, No Drawings

CHEMICAL COMPOSITIONS FOR INHIBITING NITROSATION REACTION IN TOILETRIES AND COSMETICS

CROSS REFERENCE

This application is a 371 of PCT/EP94/03264 filed Oct. 3, 1994.

The present invention relates to the use of certain compounds to inhibit nitrosation reactions (especially the formation of N-nitrosamines), to compositions comprising such compounds and to various methods of inhibiting nitrosation reactions.

N-Nitrosamines (hereinafter referred to simply as "nitrosamines") result from reaction of a nitrosating agent, such as nitrite, with a nitrosatable amino compound, for example an amine such as morpholine or dimethylamine. Most nitrosatable amines are secondary or tertiary amines, especially secondary amines. However, primary amines may be nitrosatable under certain circumstances. The properties and reactions of nitrosamines are reviewed in Kirk-Othmer "Encyclopedia of Chemical Technology" (John Wiley & Sons), Third Edition, Volume 15, pages 988 to 996.

As noted in the Kirk-Othmer reference, nitrosamines have been shown to be carcinogenic in many animal species. Accordingly, it is desirable to reduce the levels of nitrosamines in compositions with which humans and animals may come into contact, especially foodstuffs and consumer products such as toiletries, pharmaceuticals and cosmetics, but also in household and industrial products.

DE-A-3939475 (Eisenbrand) describes the use of certain amines to inhibit nitrosamine formation in cosmetics and lubricants.

WO-A-9200122 (University of Missouri) describes polymers useful for scavenging nitrosating agents, which polymers may be used in compositions to prevent nitrosating agents from reacting with any amines present to form nitrosamines.

GB-A-2274648, EP-A-0498346 and EP-A-0553800 (Albright & Wilson) describe the use of various inhibitors of nitrosamine formation, including carbonates, bicarbonates and certain phosphonates.

Wilcox et al ("Pyrroles as Effective Agents for Blocking Amine Nitrosation", Chem. Res. Toxicol. (1991), 4, 373–381) discuss ways in which nitrosamine formation may be inhibited/blocked, and state that blocking agents can be divided into three categories, viz a) those that chemically reduce the nitrosating agent (such as ascorbic acid, α-tocopherol, hydroquinone, catechols and thiols) b) those that promote deamination (such as urea and hydrazide) and c) those that covalently bind the nitrosating agent (such as certain phenols, anilines or alkenes). The authors describe various pyrroles which appear to act by the third of these mechanisms, i.e. by covalent binding of the nitrosating agent.

Schmeltz and Wenger ("2-Bromo-2-Nitropropane-1,3-Diol as a Nitrosating Agent for Diethanolamine: A Model Study", Fd Cosmet Toxicol (1979), 17, 105–109) describe a study which is alleged to show that the antimicrobial agent 2-bromo-2-nitropropane-1,3-diol (BNPD, also known as "Bronopol") caused nitrosation of diethanolamine and triethanolamine. The authors propose a mechanism by which BNPD releases nitrite ions, which are believed to be the nitrosating species, and further note that breakdown of BNPD may generate formaldehyde.

Casado et al ("Nitrite Ion as a Nitrosating Reagent. Nitrosation of Morpholine and Diethylamine in the Presence of Formaldehyde" J. Chem. Soc. Perkin Trans II (1984) pp 1963–1966) describe the kinetics of the nitrosation of morpholine and of diethylamine in the presence of formaldehyde at pH values from 6.5 to 8.2 and from 6.9 to 8.7 respectively. The authors propose a mechanism whereby the amines react with formaldehyde to form an iminium ion which then reacts with a nitrite ion to form a corresponding nitrosamine.

According to the present invention, there is provided the use of an iminium ion scavenger to inhibit nitrosation reactions.

The term "iminium ion scavenger" as used herein denotes an agent which reacts with iminium ions more readily then does a nitrosating agent such as the nitrite ion. Suitably, the iminimum ion scavenger is chosen such that at a concentration of 1M, preferably 500 mM, preferably 100 mM, suitably 10 mM, it reduces the rate of formation of nitrosamines by at least about 25%, preferably at least about 50%, preferably at least about 75%, preferably at least about 90%, especially at least about 95% in a model system comprising 44 mM morpholine, 4 mM nitrite ions and 70 mM formaldehyde at pH7 and 25° C.

Iminium ion scavengers for use in the present invention include primary amines, thiols, alcohols, carboxylic acids and salts thereof, and ammonium, alkali metal or alkaline earth metal halides (such as sodium or potassium fluoride), bicarbonates (such as sodium bicarbonate), carbonates, bisulphites (such as sodium bisulphite), sulphites, sulphates and thiosulphates. Typically they have acidic groups with a pKa of from 3.4 to 7, suitably from about 6 to 7, more suitably from about 6.2 to 6.4.

Preferably, the iminium ion scavenger is not a carbonate or bicarbonate. Preferred iminium ion scavengers include salts of di-or tricarboxylic acids such as ammonium, alkali metal or alkaline earth metal glutarates (optionally glutarates substituted with one or more $C_{1-4}$ alkyl groups), citrates, adipates, succinates and, maleates especially sodium citrate, sodium maleate, sodium adipate, sodium succinate and disodium dimethylglutarate, especially disodium 3,3-dimethylglutarate.

Preferably, the iminium ion scavenger is present at a concentration of from about 0.1 mM to about 100 mM, suitably from about 0.5 mM to about 50 mM, suitably from about 1 mM to about 25 mM, suitably from about 5 mM to about 20 mM, suitably about 10 mM. It has been found that, in some cases, increasing the iminium ion scavenger concentration above 100 mM may reduce the inhibition of nitrosation reactions.

Preferably, the iminium ion scavenger is used in a system having a pH of from about 3 to about 12, suitably from about 6 to about 8.

Preferably, the iminium ion scavenger is used in a system having a temperature between 10° C. and 100° C. Suitably it is used at ambient temperature and in systems which may be heated to above 40° C. under certain circumstances.

Suitably, the iminium ion scavenger may be used in cosmetics products such as, for example, skin creams, lotions and foundations; in toiletries such as, for example, cleansing lotions, soaps and shampoos; in dental preparations such as mouthwashes and dentifrices; and in pharmaceutical preparations such as, for example, ointments, creams, lotions, syrups and suspensions. The scavenger may also be used in household products such as waxes, polishes, liquid detergents and surface cleaners and in industrial products such as metalworking fluids, adhesives, latexes, antifoams and paints. The present invention is well suited to use in products such as these which comprise a nitrosatable amine compound and a source of nitrite ions and/or formaldehyde, such as certain antimicrobial agents (e.g. the gem-bromonitro antimicrobials such as bronopol).

The nitrosatable amine compound may be present only in trace quantities, for example as a contaminant of, for example, an amine surfactant or an amine pesticide or drug.

It may also be desirable to add the above scavengers to bulk stocks of raw materials such as bronopol and secondary amines or amine oxides, so as to inhibit formation of nitrosamines before such raw materials are formulated into products (such as the cosmetics, pharmaceutical, household and industrial products described above).

Preferably, the iminium ion scavenger is used in combination with a nitrite ion scavenger. The term "nitrite ion scavenger" as used herein denotes an agent which reacts with the nitrite ion more readily than does a nitrosatable amine such as morpholine. Suitably, the nitrite ion scavenger is chosen such that at a concentration of 1M, preferably 500 mM, preferably 100 mM, suitably 10 mM, it reduces the rate of formation of nitrosamines by at least about 25%, preferably at least about 50%, preferably at least about 75%, preferably at least about 90%, especially at least about 95% in a model system comprising 44 mM morpholine and 0.8 mM nitrite ions at pH 5 and 25° C. Typically, nitrite ion scavengers are antioxidants such as ascorbate, isoascorbate, ascorbyl peptides, ascorbyl phosphates, (such as magnesium ascorbyl phosphate from Nikko Chemicals, Japan), butylated hydroxytoluene (BHT), butylated hydroxyanisole (BHA), α-tocopherol, hydroquinone or catechol. As noted above, however, they may also be amines such as urea and hydrazide or amides such as methylsulphonamide or other compounds such as phenols, anilines and alkenes. The azide ion is also a nitrite ion scavenger, as it reacts with nitrite to form unstable nitrosyl azide which then decomposes to form nitrogen and nitrous oxide.

Use of an iminium ion scavenger in combination with a nitrite ion scavenger provides excellent inhibition of nitrosamine formation over a broad pH range (including the pH range from 3 to 12, especially the pH range from 4 to 8 typically found in cosmetics products) and over a broad temperature range (including the range of from around ambient temperature to about 45° C. to which cosmetics products are typically subjected).

The present invention further provides a composition comprising a nitrosatable compound (especially a nitrosatable amine or amide), an effective amount of an iminium ion scavenger, an effective amount of a nitrite ion scavenger and a source or sources of nitrite ions and/or formaldehyde.

The term "effective amount of an iminium ion scavenger" as used herein includes combinations of iminium ion scavengers which individually or together, are effective to inhibit nitrosation reactions. The term "effective amount of a nitrite ion scavenger" as used herein includes combinations of nitrite ion scavengers which individually or together are effective to inhibit nitrosation reactions.

Preferably, the iminium ion scavenger is present at a concentration of from about 0.1 mM to about 1M, preferably from about 0.5 mM to about 50 mM, suitably from about 1 mM to about 25 mM and reduces the rate of nitrosation reactions by at least about 25%, preferably at least about 50%, preferably at least about 90%, especially at least about 95% at pH 7 and 25° C. compared to a corresponding composition from which the scavenger is excluded.

Preferably, the nitrite ion scavenger is present at a concentration of from about 0.1 mM to about 1M, preferably from about 0.5 mM to about 50 mM, suitably from about 1 mM to about 25 mM and reduces the rate of nitrosation reactions by at least about 25%, preferably at least about 50%, preferably at least about 90%, especially at least about 95% at pH 5 and 25° C. compared to a corresponding composition from which the scavenger is excluded.

Suitably, at a combined concentration of nitrite and iminium ion scavengers of from about 0.5 mM to about 1000 mM, preferably 1 mM to 50 mM, the inhibition of nitrosation reactions is at least about 50%, preferably at least about 75%, preferably at least about 80%, preferably at about 85% and preferably at least about 90% at 25° C. between pH 5 and pH 8 compared to a corresponding composition from which the scavengers are excluded.

Suitably, the composition is a cosmetic, toiletry or pharmaceutical composition as described above.

Preferably, in such a composition, the iminium ion scavenger is sodium or potassium citrate, sodium or potassium fluoride, sodium or potassium adipate, or sodium or potassium dimethylglutarate.

Suitably, the composition comprises a gem-bromonitro antimicrobial agent such as 2-bromo-2-nitropropane-1,3-diol (BNPD; also known as "bronopol"), or another antimicrobial agent which gives rise to formaldehyde and/or nitrite, for example on decomposition.

Suitably, the composition is substantially free of phosphonic acid and/or phosphonates.

Preferably the composition has a pH of from 3 to 12, for example about 5 to 7.

Suitably, the iminium ion scavenger is present at a concentration as indicated above.

Suitably, the gem-bromonitro antimicrobial agent is present at a concentration of from about 0.0001% by weight to about 1% by weight, typically about 0.02% by weight of the composition.

In a further aspect, the present invention provides the use, as a nitrite ion scavenger as defined above, of a compound of formula I

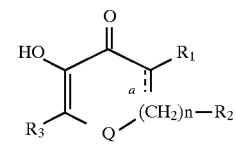

wherein n is 0 or 1 and, when n is 1, a is a bond; wherein Q is methylene, oxygen, sulphur or imino; and wherein $R_1$, $R_2$ and $R_3$ are each independently hydrogen, hydroxy, $C_{1-4}$ alkyl, $C_{1-4}$ hydroxyalkyl, $C_{1-4}$ perhaloalkyl, halo, cyano or nitro.

In one embodiment, n is 0, providing compounds of formula II

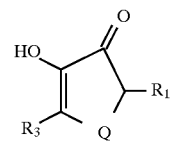

wherein Q, $R_1$ and $R_3$ are each as defined above. Preferably in compounds of formula II, Q is oxygen and $R_1$ and $R_3$ are both $C_{1-4}$ alkyl, providing 2,5-dialkyl-4-hydroxy-3(2H) furanones.

Alternatively, Q may be methylene, $R_1$ may be hydrogen or methyl and $R_3$ may be hydroxy, such as 2,3-dihydroxy-2-cyclopenten-2,3-diol-1-one (also known as "reductic acid"; see Merck Index, (1989) 11th Edition Merck & Co.

Inc., Rahway, N.J., USA, Entry No. 8134, page 1292) and 5-methyl-2,3-dihydroxy-2-cyclopenten-2,3-diol-1-one (also known as "5-methyl reductic acid"). Further examples of compounds of formula II include 2,5-dimethyl-4-hydroxy-3-furanone (CAS 3658-77-3, Beilstein 17(5), 5, 133) and 3-methylcyclopentane-1,2-dione (CAS 7657-70-8, Beilstein 7(1), 310).

In generally preferred compounds of formula I, n is 1 and therefore a is a bond, providing compounds of formula III

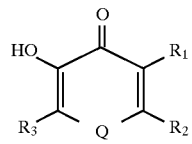

wherein Q, $R_1$, $R_2$ and $R_3$ are each as defined above.

Preferably in compounds of formula III, $R_1$, $R_2$ and $R_3$ are each independently hydrogen, methyl or hydroxymethyl. Examples of compounds of formula III are 5-hydroxy-2-hydroxymethyl-4H-pyran-4-one (also known as "kojic acid"; see Merck Index supra, Entry No. 5197, page 838), 3-hydroxy-2-methyl-4-pyrone (also known as "maltol" and available from Pfizer, USA; see Merck Index supra, Entry No. 5594, page 897), 3 hydroxy-2-ethyl-4-pyrone (also known as "ethyl maltol") and 3-hydroxy-1,2-dimethyl-4-pyridone (CAS 30652-11-0).

The compounds of formula III wherein Q is oxygen (i.e. the optionally substituted 4-hydroxy-2H-pyran-2-ones) are preferred.

The invention also provides the use of hexamethylene-tetramine (also known as "hexamine") as a nitrite ion scavenger.

There is also provided the use of a compound of formula I, II or III above to inhibit nitrosamine formation.

Suitably, the nitrite ion scavengers are used at a concentration of from about 0.01 mM to 50 mM, suitably about 10 mM.

Preferably, the nitrite ion scavengers are used in a system having a pH of from about 1 to about 12, suitably from about 3 to about 10, for example from about 4 to 8, suitably about 5.

Preferably, the nitrite ion scavenger is used in a system having a temperature of between about 10 and 100° C., suitably at ambient temperature and particularly in systems which may be heated to above 40° C. under certain circumstances.

There is also provided a composition comprising a nitrosatable compound, an effective amount of a compound of Formula I above and a source or sources of formaldehyde and/or nitrite ions.

Suitably, the composition further comprises an iminium ion scavenger as defined above.

It will be appreciated that combinations of different nitrite ion scavengers and combinations of different iminium ion scavengers may also be used. It will also be appreciated that the scavengers may be present in the form of pharmaceutically and cosmetically acceptable salts, solvates and enantiomers, where appropriate.

Suitably, the composition is a cosmetics, toiletries or pharmaceutical formulation such as those described above.

Suitably, the composition comprises a gem-bromonitro antimicrobial agent such as bronopol, or another such antimicrobial agent which releases nitrite and/or formaldehyde on decomposition.

Suitably, the composition is substantially free of phosphonic acid and/or phosphonates.

The invention further provides a concentrated composition consisting essentially of an antimicrobial agent giving rise to formaldehyde and/or nitrite ions on decomposition, an effective amount of an iminium ion scavenger and, optionally, an effective amount of a nitrite ion scavenger and, optionally, a carrier material such as water.

The term "composition consisting essentially of" as used herein denotes a composition which contains the components identified substantially free of significant quantities of other materials, for example a composition wherein the components listed make up about 75%, suitably about 90%, preferably about 99%, preferably substantially 100% of the composition by weight, volume and/or mole ratio.

The concentrated compositions according to the invention optionally further comprise suitable carriers and/or excipients. Advantageously the compositions may incorporate at least one buffering agent to minimise the fall of pH which may otherwise occur after dilution of the concentrated composition. The concentrated compositions may be provided in the form of packs containing one or more discrete units of an appropriate weight or volume for batch or unit dosing.

Concentrated compositions according to the invention may comprise substantially anhydrous mixtures of each of the components mentioned hereinbefore, optionally combined with suitable non-aqueous carriers or excipients. Such compositions may be in the form of, for example, powders, compressed tablets, capsules, or anhydrous solutions, pastes or suspensions. The compositions may be stored under anhydrous conditions for example in dessicators, hermetically sealed containers such as sachets, or in evacuated vials, ampoules or pump packs.

Concentrated solvated compositions, optionally combined with suitable carriers or excipients, may be packaged and maintained prior to use. They may be in the form of, for example, solutions, suspensions, emulsions, pastes or gels. Suitable solvents include water, ethyl and/or propyl alcohol, diethylene and/or dipropylene glycol and/or polyethylene glycol.

Where the composition comprises water it may be preferable to add a proportion of a polar organic co-solvent such as propylene or polyethylene glycol to prevent the composition freezing when, for example, the composition is stored at low temperatures.

Suitably, the composition comprises both an effective amount of iminium ion scavenger and an effective amount of a nitrite ion scavenger.

In one embodiment, the antimicrobial agent is a gem-bromonitro antimicrobial such as bronopol.

Suitably in such compositions, the antimicrobial agent is present in a molar ratio of from about 1:0.05 to 1:100, suitably from about 1:0.1 to 1:50, preferably from about 1:1 to 1:20, preferably from about 1:5 to 1:15, for example about 1:10, relative to the iminium ion scavenger or combination of iminium ion scavengers.

Suitably, the antimicrobial agent is present in a molar ratio of from about 1:0.05 to 1:100, suitably from about 1:0.1 to 1:50, preferably from about 1:1 to 1:20, preferably from about 1:5 to 1:15, for example about 1:10, relative to the nitrite ion scavenger or combination of nitrite ion scavengers.

Suitably, the nitrite and iminium ion scavengers used are the preferred compounds described above.

The invention also provides a composition consisting essentially of an antimicrobial agent giving rise to formaldehyde and/or nitrite ions on decomposition, an effective amount of hexamethylene-tetramine or a compound of formula I and, optionally, an iminium ion scavenger and, optionally, a carrier material, such as water.

The invention further provides a composition consisting essentially of an iminium ion scavenger or combination of iminium ion scavengers, a nitrite ion scavenger or a combination of nitrite ion scavengers and, optionally, a preservative and, optionally, a carrier material, such as water.

Suitably, the iminium ion scavenger and nitrite ion scavenger are present in a molar ratio of from about 1:50 to 50:1, suitably from about 1:10 to 10:1, preferably from about 1:5 to 5:1, for example about 1:1.

As noted above, it may also be desirable to include nitrite and/or iminium ion scavengers in nitrogenous raw materials which are susceptible to nitrosation reactions, so as to reduce or prevent the occurrence of such reactions during storage of the raw material. The raw materials may themselves be nitrosatable, or may be contaminated with nitrosatable compounds which may, for example, be present as by-products from the manufacturing process or as decomposition products resulting from decomposition of the raw material over time.

Thus, the invention further provides a composition consisting essentially of a nitrogenous raw material comprising a nitrosatable compound, an effective amount of an iminium ion scavenger and, optionally, an effective amount of a nitrite ion scavenger and, optionally, a carrier material such as water and, optionally, a preservative such as formaldehyde or bronopol. Preferably, the composition comprises effective amounts of both iminium and nitrite ion scavengers.

The presence of the iminium ion scavenger and, where present, the nitrite ion scavenger, will inhibit nitrosation reactions during storage of the raw material. Moreover, when the material is used, for example in formulating a cosmetics, toiletries, pharmaceutical, household or industrial product of the type described above, the scavenger(s) will automatically be incorporated into the final formulation at a suitable mole ratio relative to the nitrosatable compound.

The invention also provides a composition consisting essentially of a nitrogenous raw material, an effective amount of hexamethylene tetramine or a compound of formula I above, and, optionally, an effective amount of an iminium ion scavenger and, optionally, a carrier material such as water and, optionally, a preservative such as formaldehyde or bronopol.

Suitably, the nitrogenous material is an amine or amide, suitably an amine or amide surfactant, for example a primary amine surfactant such as a monoethanolamine salt of lauryl sulphonic acid, an amide surfactant such as cocamide diethanolamide or a tertiary amine surfactant such as a triethanolamine salt of laurylsulphonic acid, which may all contain nitrosatable amines as, for example, byproducts or decomposition products.

Nitrosatable surfactants include anionic surfactants such as the triethanolamine salt of $C_{12}/C_{14}$ fatty alcohol sulphate, triethanolamine salt of lauryl ether sulphonate, triethanolamine/diethanolamine salt of dodecylbenzene sulphonate, triethanolamine/ diethanolamine salt of cetyl phosphate, triethanolamine salt of dioctylsulphosuccinate, sodium-N-lauroyl sarcosinate, sodium-N-methyl-N-alkyl taurate, and sodium-N-octadecyl succinamate; amphoteric surfactants such as cocoamphocarboxylglycinate and cocoamidopropylbetaine; nonionic surfactants such as tallow amine ethoxylate, lauryl dimethylamine oxide and other amine oxides and coconut fatty acid diethanolamide; and quaternary surfactants such as stearyl dimethyl benzyl ammonium chloride.

The nitrosatable amine may also be a sunscreen compound such as one based on para-amino-benzoic acid, or a thickening agent (eg a carbomer-type acrylic acid polymer) which has been chemically modified with amines. It may also be a nitrosatable pesticide, e.g. a herbicide such as acifluorfen, benefin, dinitromine, dinoseb, ethalfluralin, isopropalin, nitrolin, nitrofen, oxyzalin, oxyfluorofen, pendimethalin, prodiamine, profluralin, prosulfalin or trifluralin, or a nitrosatable drug such as a tetracycline.

Suitably in such compositions, the nitrosatable amine is present in a molar ratio of from about 1:0.01 to 1:100, suitably from about 1:0.05 to 1:50, preferably from about 1:0.1 to 1:10, preferably about 1:1, relative to the iminium ion scavenger or combination of iminium ion scavengers.

Suitably, the nitrosatable amine is present in a molar ratio of from about 1:0.01 to 1:100, suitably from about 1:0.05 to 1:50, preferably from about 1:0.1 to 1:10, for example about 1:1, relative to the nitrite ion scavenger or combination of nitrite ion scavengers.

The nitrite and iminium ion scavengers of the present invention may also be used in foodstuffs such as cooked meats, cereal products and beverages to inhibit nitrosation reactions during processing or storage. Thus, there is further provided a method of inhibiting nitrosation reactions in a foodstuff by applying an iminium ion scavenger to the foodstuff during processing, manufacture or storage. Preferably a nitrite ion scavenger is also applied. There is also provided a foodstuff material comprising an effective amount of a nitrite and an iminium ion scavenger and a source of nitrite ions.

The nitrite and iminium ion inhibitors of the present invention can also be used to inhibit nitrosation in vivo. Nitrosamines can form in the digestive tracts of animals as a result inter alia of reactions of foodstuffs, food additives and pharmaceuticals. For example, the tetracyclines such as oxytetracycline and aminopyrine contain N-nitrosatable groups which may react with nitrites in the stomach to form nitrosamines.

The present invention further provides a method of inhibiting nitrosamine formation in an animal by administering a nitrite ion scavenger or an iminium ion scavenger as defined above. Suitably both a nitrite ion scavenger and an iminium ion scavenger are administered. The scavengers may be administered by any suitable means, for example orally, enterally or parenterally. Oral administration is preferred. Suitably the animal is a mammal such as man.

The invention further provides a pharmaceutical composition comprising a nitrite ion scavenger and/or an iminium ion scavenger for use in the inhibition of nitrosamine formation in an animal. Suitably, the animal is a mammal such as man.

There is further provided the use of a nitrite ion scavenger and/or an iminium ion scavenger in the inhibition of nitrosation reactions in an animal, and the use of a nitrite ion scavenger and/or an iminium ion scavenger in the manufacture of a medicament for the inhibition of nitrosation reactions in an animal.

The invention further provides a pharmaceutical composition comprising a nitrosatable medicament such as a tetracycline, an iminium ion scavenger and, optionally a nitrite ion scavenger, together with a pharmaceutically acceptable diluent or carrier.

The therapeutic compositions of the present invention may take the form of any of the known pharmaceutical compositions for oral, rectal, parenteral or topical administration. The compositions may be formulated in a manner known to those skilled in the art so as to give a controlled release of the compounds of the present invention. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacists' art.

Tablets may be prepared by mixing the active compound with an inert diluent, such as lactose or calcium phosphate, in the presence of disintegrating agents, for example maize starch, and lubricating agents, for example magnesium stearate, and tableting the mixture by known methods. Such tablets may if desired be provided with enteric coatings by known methods, for example by the use of cellulose acetate phthalate. Similarly capsules, for example hard or soft gelatin capsules containing the active compound with or without added excipients, may be prepared by conventional means and, if desired, provided with enteric coatings in a known manner. Enteric coated compositions of the invention may be advantageous, depending on the nature of the active compound. The tablets and capsules may conveniently each contain 1–500 mg of the active medicament. Other compositions for oral administration include, for example, aqueous suspensions in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with semi-synthetic glycerides or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the active compound is dispersed so that it is held in contact with the skin in order to administer the medicament transdermally. Alternatively the active medicament may be dispersed in a cream or ointment base.

The nitrite and iminium ion scavengers of the present invention can also be used during the preparation of nitrosatable amine materials such as nitrosatable surfactants, herbicides and pharmaceuticals, for example in the manner described in European Patent Publication No. 498346 (Albright & Wilson).

Thus the present invention further provides a method of stabilising a nitrosatable amine material to inhibit the formation of nitrosamines by adding to the material an effective amount of an iminium ion scavenger and optionally a nitrate ion scavenger as defined above. The scavengers may be added either before, during or after the preparation of the amine material.

The nature of the present invention will be better understood with reference to the following non-limiting comparative tests and examples. In these tests and examples, square brackets are used to denote concentration, and the subscript "0" is used to denote initial concentration. Thus, for example [Morpholine] denotes concentration of morpholine and $[Morpholine]_0$ denotes initial concentration of morpholine (ie the concentration at the start of the experiment).

Comparative Test A

The effect of various iminium ion scavengers on the formation of nitrosamines in a typical bath gel-type formulation was investigated. The gel (Gel 1) had the following composition:

| Gel 1 | |
| --- | --- |
| Component | Concentration (% w/v) |
| Sodium Laureth Sulphate | 24.0 |
| Cocamide DEA | 1.5 |
| Sodium Chloride | 6.0 |
| Dichlorobenzyl Alcohol | 0.1 |
| Propylene Glycol | 0.74 |
| Water | 67.95 |

Each inhibitor was tested in Gel 1 at a final concentration of 10 mM and 100 mM. In each case portions (44.5 g and 39.5 g respectively) of the gel were mixed with 50:50 M:M morpholine:diethanolamine (5 cm$^3$; 1M) and an aqueous solution of the inhibitor (0.5 cm$^3$ and 5 cm$^3$ respectively of a 1M solution). The resulting mixture was stirred for about an hour, after which an aqueous solution of bronopol (0.5 cm$^3$; 0.1M) was added and the resulting mixture was stirred for a further hour. 1 g Aliquots were then transferred to amber ampoules and stored variously at 22° C. and at 40° C. Each aliquot was analysed at 28 days and 56 days and, where possible, at 84 days and 196 days, to determine both nitrite and total N-nitrosamine concentrations. The method of Challis and Trew was used (D F Trew, PhD Thesis, The Open University, 1992). According to this method, a portion of each sample was injected into a solution of hydrobromic acid/acetic acid (45% w/v; 10 cm$^3$) in boiling n-propyl acetate (50 cm$^3$) to cause any nitrite and N-nitrosamine to react to release nitric oxide (NO). The nitric oxide released was swept out of the solvent by a nitrogen stream and measured with a chemiluminescence detector calibrated with a standard solution of N-nitrosodiisopropylamine, to give total nitrite and N-nitrosamine content. The procedure was repeated with a further portion of each sample after pretreatment of the sample with approximately 100 mg sulphamic acid to destroy any nitrite present. The nitrite content was obtained from the difference between the two determinations.

Results obtained using sodium citrate and potassium fluoride as inhibitors at 22° C. are shown in Table 1, and results obtained using sodium citrate, potassium fluoride, ammonium bicarbonate, sodium bicarbonate and 2-amino-2-methylpropanol as inhibitors at 40° C. are shown in Table 2.

TABLE 1

N-nitrosamine ($R_2NNO$) inhibition in bath gel (Gel 1) with 5 mM morpholine and 5 mM diethanolamine at 22° C. (pH 7)
Initial bronopol concentration = 1 mM

| Inhibitor (concentration in brackets) | [nitrite] ppm NO | [$R_2NNO$] ppb NO | % inhibition | [nitrite] ppm NO | [$R_2NNO$] ppb NO | % inhibition |
|---|---|---|---|---|---|---|
| TIME | 28 days | | | 56 days | | |
| trisodium citrate (10 mM) | 2.3 | 90 | 46 | 4.9 | 240 | 17 |
| trisodium citrate (100 mM) | 4.5 | 120 | −9 | 4.9 | 190 | 17 |
| potassium fluoride (10 mM) | 2.8 | 150 | 11 | 5.8 | 290 | −4 |
| potassium fluoride (100 mM) | 1.3 | 210 | −90 | 5.8 | 230 | 0 |
| TIME | 84 days | | | 196 days | | |
| trisodium citrate (10 mM) | 6.4 | 275 | 43 | 6.9 | 240 | 70 |
| trisodium citrate (100 mM) | 6.7 | 310 | 6 | 7.4 | 140 | 82 |
| potassium fluoride (10 mM) | | | | 6.4 | 260 | 68 |
| potassium fluoride (100 mM) | | | | 7.2 | 230 | 71 |

TABLE 2

N-nitrosamine ($R_2NNO$) inhibition in bath gel (Gel 1) with 5 mM morpholine and 5 mM diethanolamine at 40° C. (pH 7)
Initial bronopol concentration = 1 mM

| Inhibitor (concentration in brackets) | [nitrite] ppm NO | [$R_2NNO$] ppb NO | % inhibition | [nitrite] ppm NO | [$R_2NNO$] ppm NO | % inhibition |
|---|---|---|---|---|---|---|
| TIME | 28 days | | | 56 days | | |
| ammonium bicarbonate (10 mM) | 12 | 290 | 60 | 13 | 560 | 53 |
| ammonium bicarbonate (100 mM) | 19 | 320 | 48 | 17 | 530 | 56 |
| ammonium bicarbonate (10 mM) | 8.8 | 350 | 52 | 12 | 400 | 67 |
| ammonium bicarbonate (100 mM) | 12 | 510 | 18 | 11 | 480 | 60 |
| trisodium citrate (10 mM) | 10 | 120 | 84 | 10 | 210 | 82 |
| trisodium citrate (100 mM) | 8.8 | 150 | 76 | 10 | 160 | 86 |
| potassium fluoride (10 mM) | 7.2 | 190 | 74 | 8.4 | 180 | 85 |
| potassium fluoride (100 mM) | 7.3 | 180 | 71 | 10 | 230 | 81 |
| n-Pr-gallate (10 mM) | 4.9 | 270 | 63 | 3.7 | 520 | 57 |
| 2-amino-2-methyl-propanol (10 mM) | 10 | 310 | 57 | 11 | 430 | 64 |
| 2-amino-2-methyl-propanol (100 mM) | 13 | 130 | 79 | 13 | 630 | 48 |
| TIME | 84 days | | | 196 days | | |
| trisodium citrate (10 mM) | 10.3 | 237 | 88 | 10 | 230 | 91 |
| trisodium citrate (100 mM) | 6.4 | 185 | 91 | 11 | 210 | 93 |
| potassium fluoride (10 mM) | | | | 11 | 180 | 85 |
| potassium fluoride (100 mM) | | | | 12 | 580 | 82 |

Comparative Test B

Solutions (2 cm$^3$) of various iminium ion scavengers (10 mM), morpholine (10 mM) and bronopol (10 mM) in 50% (v/v) aqueous acetonitrile were incubated at 70° C. for 24 hours and then assayed for total nitrosamines by the method described under Test A above. Results are set out in Table 3.

TABLE 3

| inhibitor | pK$_A$ | % inhibition |
| --- | --- | --- |
| sodium acetate | 4.75 | 29 |
| disodium succinate | 5.64 (pK$_2$) | 44 |
| aminomethylsulphonic acid | 5.75 | 69 |
| disodium maleate | 6.23 (pK$_2$) | 74 |
| trisodium citrate | 6.4 (pK$_3$) | 73 |
| disodium hydrogen phosphate | 7.1 (pK$_2$) | 46 |

Comparative Test C

The effect of sodium citrate on the formation of nitrosamines in Gel 1 was investigated as follows:

300 mg of Gel 1 was mixed with an aliquot (600 μl) of morpholine (2.5M) and diethanolamine in absolute ethanol and the resulting mixture was stirred for one hour. The mixture was then adjusted to pH 7 with aqueous acetic acid (1M) and/or aqueous sodium hydroxide (0.1M) and stirred for a further hour. An aliquot of aqueous bronopol (300 μl; 1M) was then added and the resulting mixture stirred for a further hour. The mixture was then divided into four 60 cm$^3$ portions and to each portion was added either:
1. water (1200 μl);
2. aqueous sodium citrate (60 μl; 1M) and water (1140 μl);
3. aqueous sodium citrate (600 μl; 1M) and water (600 μl); or
4. aqueous sodium citrate (600 μl; 1M) and aqueous glycerol (600 μl; 1M).

The samples were stored in 5 cm$^3$ amber ampoules at 40° C. and were analysed for nitrite and total nitrosamines by the method described under Test A above. Analyses were carried out variously at the start of the experiment (0 days) and at 28, 56 and 84 days. Results are set out below in Table 4.

TABLE 4

N-Nitrosamine (R$_2$NNO) Inhibition in bath gel (Gel 1) at 40° C. by trisodium citrate

| Time (days) | [trisodium citrate] mM | [nitrite] ppm NO | [R$_2$NNO] ppb NO | inhibition % |
| --- | --- | --- | --- | --- |
| 0 | 0 | 0.25 | | |
| 0 | 1 | 0.24 | | |
| 0 | 10 | 0.32 | | |
| 0 | 10a | 0.31 | | |
| 28 | 0 | 6.8 | 820 | |
| 28 | 1 | 15.9 | 700 | 15 |
| 28 | 10 | 13.9 | 670 | 18 |
| 28 | 10a | 15.4 | 700 | 15 |
| 56 | 0 | 10.9 | 1650 | |
| 56 | 1 | 11.1 | 1100 | 23 |
| 56 | 10 | 11.9 | 1040 | 37 |
| 56 | 10a | 11.1 | 1100 | 33 |
| 84 | 0 | 9.2 | 2330 | |
| 84 | 1 | 9.8 | 1670 | 39 |
| 84 | 10 | 11.7 | 1440 | 38 |
| 84 | 10a | 11.8 | 1590 | 32 |

$^a$glycerol included at 10 mM

Comparative Test D

The procedure of Test C above was repeated with the modification that instead of Gel 1, the following cream base (Cream Base 1) was used:

Cream Base 1

| Component | Concentration (% w/v) |
| --- | --- |
| Steareth - 5 Stearate | 2.0 |
| Steareth - 10 | 1.6 |
| Glyceryl Stearate | 2.0 |
| Cetyl Alcohol | 1.2 |
| Mineral Oil | 3.0 |
| Dimethicone | 2.0 |
| Water | to 100 |

10 cm$^3$ clear glass ampoules were used for sample storage (in place of the amber ampoules described in Test C). Results are set out below in Table 6.

TABLE 6

Total Nitrosamines (R$_2$NNO) in cream base (Cream Base 1) with trisodium citrate

| Time (days) | [Trisodium Citrate] mM | Temp °C. | pH | [Nitrite] ppm NO | [R$_2$NNO] ppb NO | Inhibition % |
| --- | --- | --- | --- | --- | --- | --- |
| 28 | 0 | 22 | 6.2 | 2.2 | 78 | |
| 28 | 10 | 22 | | 2.3 | 82 | 0 |
| 28 | 0 | 40 | 5.9 | 4.0 | 340 | |
| 28 | 10 | 40 | 6.7 | 6.1 | 185 | 47 |
| 56 | 0 | 40 | 5.7 | 4.4 | 1020 | |
| 56 | 10 | 40 | 6.7 | 9.6 | 390 | 62 |
| 84 | 0 | 22 | 6.2 | 0.98 | 230 | |
| 84 | 10 | 22 | 6.7 | 1.5 | 200 | 13 |
| 84 | 0 | 40 | 5.6 | 3.1 | 1830 | |
| 84 | 10 | 40 | 6.2 | 8.0 | 480 | 76 |

Comparative Test E

The procedure of Test C above was repeated with the modification that disodium 3,3-dimethylglutarate was used in place of sodium citrate. Results are set out below in Table 7.

TABLE 7

N-Nitrosamine Inhibition in bath gel (Gel 1) by disodium 3,3-dimethylglutarate (Na$_2$DMG)

| Time (days) | [Na$_2$DMG] mM | Initial bronopol conc mM | Initial pH | Temp °C. | pH | [Nitrite]† ppm NO | [R$_2$NNO]* ppb NO | Inhibition % |
|---|---|---|---|---|---|---|---|---|
| 28 | 0 | 1 | 6.8 | 40 | 6.0 | 16 | 1460 | |
| 28 | 10 | 1 | 6.8 | 40 | 5.4 | 4.7 | 300 | 79 |
| 28 | 0 | 1 | 6.8 | 22 | 6.6 | 6.1 | 130 | |
| 28 | 10 | 1 | 6.8 | 22 | 5.4 | 0.57 | 31 | 77 |
| 28 | 0 | 10 | 4.8 | 22 | 4.7 | 0.45 | 94 | |
| 28 | 10 | 10 | 4.8 | 22 | 4.8 | 0.60 | 54 | 42 |
| 28 | 0 | 1 | 4.8 | 22 | 4.8 | 2.5 | 30 | |
| 28 | 10 | 1 | 4.8 | 22 | | 2.1 | 28 | 7 |
| 28 | 0 | 1 | 4.8 | 40 | 4.8 | 2.7 | 570 | |
| 28 | 10 | 1 | 4.8 | 40 | 4.7 | 0.8 | 550 | 4 |
| 56 | 0 | 1 | 6.8 | 40 | 6.4 | 19 | 8390 | |
| 56 | 10 | 1 | 6.8 | 40 | 5.4 | 3.1 | 1670 | 80 |
| 56 | 0 | 1 | 6.8 | 22 | 6.7 | 8.8 | 380 | |
| 56 | 10 | 1 | 6.8 | 22 | 5.4 | 0.98 | 61 | 84 |
| 56 | 0 | 10 | 4.8 | 22 | 4.7 | 0.97 | 170 | |
| 56 | 10 | 10 | 4.8 | 22 | 4.8 | 0.87 | 125 | 26 |
| 56 | 0 | 1 | 4.8 | 22 | | 0.25 | 43 | |
| 56 | 10 | 1 | 4.8 | 22 | | 0.3 | 43 | |
| 56 | 0 | 1 | 4.8 | 40 | | 1.6 | 1090 | |
| 56 | 10 | 1 | 4.8 | 40 | | 0.9 | 760 | 31 |
| 84 | 0 | 1 | 6.8 | 40 | | 12 | 6280 | |
| 84 | 10 | 1 | 6.8 | 40 | | 4.6 | 2580 | 59 |
| 84 | 0 | 1 | 6.8 | 22 | | 11 | 560 | |
| 84 | 10 | 1 | 6.8 | 22 | | 0.95 | 85 | 85 |
| 84 | 0 | 10 | 4.8 | 22 | | 1.6 | 260 | |
| 84 | 10 | 10 | 4.8 | 22 | | 1.6 | 310 | −19 |

†Initial nitrite concentration in range 0.30–0.49 ppm NO;
*Initial N-Nitrosamine concentration below 20 ppb NO Comparative Test F The effect of a combination of sodium citrate and ascorbic acid on the formation of nitrosamines in Gel 1 was investigated. The procedure of Test C was used modified in that bronopol concentration was increased to 10 mM, all tests were carried out at 40° C. and ascorbic acid was included at 10 mM in half of the samples. Results are set out below in Table 8.

TABLE 8

N-Nitrosamine (R$_2$NNO) Inhibition in Bath Gel (Gel 1) by Trisodium Citrate and Ascorbic Acid at 40° C. and Initial pH of 5

| Time (days) | [ascorbic acid]$_0$ mM | pH | [Nitrite] ppm NO | [R$_2$NNO]* ppm NO | inhibition % |
|---|---|---|---|---|---|
| 0 | 0 | | 0.95 | <0.02 | |
| 0 | 10 | | 0.22 | <0.02 | |
| 28 | 0 | 4.9 | 17 | 28 | |
| 28 | 10 | 5.0 | 0.9 | 11.4 | 59 |
| 56 | 0 | 4.9 | 17 | 75 | |
| 56 | 10 | 5 | 0 | 14 | 81 |

* = Initial nitrosamine concentration below 20 ppb NO

Comparative Test G

An aliquot (500 μl) of a solution of morpholine (1M) and diethanolamine (1M) in water plus an aliquot (2 cm$^3$) of a solution of sodium citrate (0.5M) and ascorbic acid (0.5M), adjusted to the required pH with aqueous acetic acid (1M) and aqueous sodium hydroxide (2M), were added sequentially to a sample (100 g) of the bath gel (Gel 1) described above. The resulting mixture was stirred for about one hour. The pH was further adjusted with aqueous acetic acid (1M) and aqueous sodium hydroxide (2M). Bronopol (1 cm$^3$; 0.1M) was added, the resulting mixture was stirred for a further hour, then transferred to 5 cm$^3$ amber ampoules and stored for up to 84 days at either 22° C. or 40° C. As a control, this procedure was repeated with the modification that water (2 cm$^3$) was added in place of the solution of sodium citrate and ascorbic acid, after pH adjustment and addition of bronopol. Each mixture was analysed as described in Test A above at 28 days and 56 days and, where possible, at 84 days, to determine both nitrite and total N-nitrosamine concentrations. The results are set out below in Table 9 (for samples stored at 22° C.) and Table 10 (for samples stored at 40° C.).

TABLE 9

Nitrosamine (R₂NNO) inhibition by trisodium citrate (10 mM) and ascorbic acid (10 mM) in bath gel (Gel 1) with 5 mM morpholine and 5 mM diethanolamine at 22° C.
Initial bronopol concentration = 1 mM

| Time (days) | Inhibitors (concentration in brackets) | pH | [nitrite] ppm NO | [$R_2NNO$] ppm NO | % inhibition[a] |
|---|---|---|---|---|---|
| 28 | None (control) | 7 | 6.5 | 110 | |
| 28 | trisodium citrate (10 mM) + ascorbic acid (10 mM) | 7 | 5.1 | 100 | 9 |
| 28 | None (control) | 6 | 0.6 | 42 | |
| 28 | trisodium citrate (10 mM) + ascorbic acid (10 mM) | 6 | 1.0 | 114 | −171 |
| 28 | None (control) | 5 | 0.16 | 33 | |
| 28 | trisodium citrate (10 mM) + ascorbic acid (10 mM) | 5 | 0.14 | 160 | −38 |
| 56 | None (control) | 7 | 9.7 | 270 | |
| 56 | trisodium citrate (10 mM) + ascorbic acid (10 mM) | 7 | 1.5 | 130 | 52 |
| 56 | None (control) | 6 | 1.5 | 51 | |
| 56 | trisodium citrate (10 mM) + ascorbic acid (10 mM) | 6 | 0.21 | 78 | −53 |
| 56 | None (control) | 5 | 0.23 | 44 | |
| 56 | trisodium citrate (10 mM) + ascorbic acid (10 mM) | 5 | 0.22 | 69 | −57 |
| 84 | None (control) | 7 | 9.0 | 420 | |
| 84 | trisodium citrate (10 mM) + ascorbic acid (10 mM) | 7 | 1.1 | 100 | 76 |
| 196 | None (control) | 7 | 8.3 | 830 | |
| 196 | trissodium citrate (10 mM) + ascorbic acid (10 mM) | 7 | 0.13 | 134 | 83 |
| 196 | None (control) | 6 | 2.3 | 200 | |
| 196 | trisodium citrate (10 mM) + ascorbic acid (10 mM) | 6 | 1.9 | 55 | 72 |
| 196 | None (control) | 5 | 0.5 | 80(±20) | |
| 196 | trisodium citrate (10 mM) + ascorbic acid (10 mM) | 5 | 0 | 50(±25) | 38 |

[a]Relative to line above

TABLE 10

Nitrosamine (R₂NNO) inhibition by trisodium citrate (10 mM) and ascorbic acid (10 mM) in bath gel (Gel 1) with 5 mM morpholine and 5 mM diethanolamine at 40° C.
Initial bronopol concentration = 1 mM

| Time (days) | Inhibitors (concentration in brackets) | pH | [nitrite] ppm NO | [$R_2NNO$] ppm NO | % inhibition[a] |
|---|---|---|---|---|---|
| 28 | None (control) | 7 | 15 | 710 | |
| 28 | trisodium citrate (10 mM) + ascorbic acid (10 mM) | 7 | 0.39 | 97 | 86 |
| 28 | None (control) | 6 | 6 | — | |
| 28 | trisodium citrate (10 mM) + ascorbic acid (10 mM) | 6 | 4.5 | 100 | — |
| 28 | None (control) | 5 | 0.39 | 110 | |
| 28 | trisodium citrate (10 mM) + ascorbic acid (10 mM) | 5 | 0.04 | 33 | 70 |
| 56 | None (control) | 7 | 12.7 | 1330 | |
| 56 | trisodium citrate (10 mM) + ascorbic acid (10 mM) | 7 | 0.2 | 170 | 86 |
| 56 | None (control) | 6 | 1.5 | 930 | |
| 56 | trisodium citrate (10 mM) + ascorbic acid (10 mM) | 6 | 0.2 | 90 | 90 |
| 56 | None (control) | 5 | 2.22 | 290 | |
| 56 | trisodium citrate (10 mM) + ascorbic acid (10 mM) | 5 | 0 | 170 | 41 |
| 84 | None (control) | 7 | 11.4 | 1710 | |

TABLE 10-continued

Nitrosamine ($R_2NNO$) inhibition by trisodium citrate (10 mM) and
ascorbic acid (10 mM) in bath gel (Gel 1) with 5 mM morpholine and
5 mM diethanolamine at 40° C.
Initial bronopol concentration = 1 mM

| Time (days) | Inhibitors (concentration in brackets) | pH | [nitrite] ppm NO | [$R_2NNO$] ppm NO | % inhibition[a] |
|---|---|---|---|---|---|
| 84 | trisodium citrate (10 mM) + ascorbic acid (10 mM) | 7 | 0.02 | 130 | 92 |
| 84 | None (control) | 6 | 3.6 | 870 | |
| 84 | trisodium citrate (10 mM) + ascorbic acid (10 mM) | 6 | 0.6 | 140 | 83 |
| 84 | None (control) | 5 | 0.18 | 660 | |
| 84 | trisodium citrate (10 mM) + ascorbic acid (10 mM) | 5 | 0.2 | 62 | 90 |
| 196 | None (control) | 7 | 12.6 | 4500 | |
| 196 | trisodium citrate (10 mM) + ascorbic acid (10 mM) | 7 | 0.06 | 130 | 97 |
| 196 | None (control) | 6 | 2.7 | 1550 | |
| 196 | trisodium citrate (10 mM) + ascorbic acid (10 mM) | 6 | 0.01 | 100 | 93 |
| 196 | None (control) | 5 | 0.7 | 1020 | |
| 196 | trisodium citrate (10 mM) + ascorbic acid (10 mM) | 5 | 0.02 | 40 | 95 |

[a]Relative to line above
[a]Relative to control (see line above in table)

Test H

The kinetics of morpholine nitrosation in the presence of formaldehyde and nitrite ions were investigated as follows:

Reactant solutions containing morpholine (11–88 mM), formaldehyde (0–140 mM), sodium nitrite (1–4 mM) and inhibitors where relevant in 20% (v/v) ethanol: water at the required pH (by adjustment with perchloric acid (5M) or sodium hydroxide (2M)) and contained in sealed, amber glass ampoules (5 cm$^3$) were placed in a thermostatted bath at 25° C. At regular time intervals, ampoules were withdrawn and cooled in ice. An aliquot (1 cm$^3$) was added to aqueous sulphamic acid (1 cm$^3$; 1M) containing N-nitrosopiperidine (100 μl, 0.7–1.4 mM) as internal standard and pyrrolidine (100 μl, 100 mM) as an artifact control. After thorough mixing and standing for approximately 10 minutes, this solution was extracted with dichloromethane (2 cm$^3$), dried over sodium sulphate and then assayed for nitrosamines by capillary gas chromatography (isothermally at 110° C. on a BP20 (SGE, 12 m×0 33 mm id) silica column). Under these conditions, the retention times (with base-line separation) were N-nitrosopiperidine (2.3 minutes) N-nitrosopyrrolidine (2.8 minutes) and N-nitrosomorpholine (3.5 minutes).

N-Nitrosomorpholine was quantitated by peak area comparison against the N-nitrosopiperidine internal standard. There was no evidence of artifactual formation of N-nitrosopyrrolidine. The limit of detection was approximately 1 μM N-nitrosomorpholine and the reproducibility for duplicate injections was ±2–5%.

N-Nitrosomorpholine formation was usually monitored over the initial 6% reaction only. Initial reaction rates ($r_o$) were obtained from the slopes of N-nitrosomorpholine concentration versus time plots. These were usually linear or very slightly curved. The error in $r_o$ values was estimated to be ±10%. Since morpholine and HCHO were in excess, pseudo first order rate coefficients ($k_o$) were obtained from $r_o$ via equation I.

$$r_o = k_o[\text{NaNO}_2] \qquad \text{I}$$

The studies were carried out at pH 5–7 and 25° C. using an approximately 10-fold excess of morpholine, low concentrations (1–4 mM) of sodium nitrite and varying amounts of formaldehyde up to 70 mM (2100 ppm). Initial rates ($r_o$=d[N-nitrosomorpholine]/dt) of N-nitroso-morpholine formation were obtained from data over the first 6% of reaction and converted into pseudo first-order initial rate coefficients ($k_o$) via equation I. Results are set out in Table 12.

TABLE 12

Variation of $k_0$ with [trisodium citrate] for
the nitrosation of morpholine at pH 7 and 25° C.
[Morpholine]$_0$ = 44 mM, [formaldehyde]$_0$ = 70 mM, [sodium nitrite]$_0$ = 4 mM.

| 10$^3$ [trisodium citrate] mM | 10$^6$k$_o$ s$^{-1}$ |
|---|---|
| 0 | 4.0 |
| 0.5 | 3.6 |
| 1 | 2.7 |
| 10 | 1.5 |
| 25 | 1.1 |
| 100 | 1.2 |
| 100[a] | 1.9 |
| 1000 | 0.8 |

[a]In presence of 100 mM ascorbic acid.

Further kinetic studies were carried out by taking initial rate measurements in 80% (v/v) aqueous-ethanol acetate buffers (100 mM) at pH 5 and at pH 7 and 25° C. using 44 mM morpholine and 0.8 mM sodium nitrite. Results are set out in Tables 13 and 14.

The degree of colouration in samples inhibited with nitrite scavengers was estimated by measuring the area under the visible absorption curve above 400 nm. The Spectra were recorded over the range 350–700 nm in quartz curvettes (1 cm) on a Cecil 5000 spectrophotometer. The area under the absorbance curve was measured by making a photocopy of the spectrum, cutting out the relevant portion and weighing on a 5 decimal place balance. Figures are given in Tables 13 as "colour index".

TABLE 13

Inhibition of N-nitrosomorpholine formation by nitrate scavengers in 80% (v/v) aqueous -ethanol acetate buffers (100 mM) at pH5 and 25° C.; [Morpholine]$_0$ = 40 mM; [sodium nitrite]$_0$ = 0.8 mM.

| Scavenger/Inhibitor (concentration as given by footnote) | $\dfrac{10^6 k_0}{s^{-1}}$ | colour index |
|---|---|---|
| None (control) | 1.2 | — |
| Maltol[a] | 0.18 | 72 |
| Ethyl maltol[a] | 0.62 | 174 |
| 3-Hydroxypyridine | 1.1 | 19 |
| Magnesium ascorbyl-3-phosphate[b] | 0.12 | 33 |
| Ascorbyl peptide[b] (available from Brooks Industries under the trade name "Vitazyme C") | <0.01 | 108 |
| 3-Methylcyclopentane-1,2-dione[a] | 0.16 | 68 |
| Isoascorbic acid[a] | <0.01 | 46 |
| Kojic acid[a] | 0.51 | |
| 2,5-Dimethyl-4-hydroxy-3-furanone[a] | 0.49 | 5 |

[a]10 mM
[b]10 meq

TABLE 14

Inhibition of N-nitrosomorpholine formation via the iminium ion pathway at 25° C. by neutral salts: Initial pH = 7; [Morpholine]$_0$ = 44 mM; [formaldehyde]$_0$ = 70 mM; [sodium nitrite]$_0$ = 4 mM

| Inhibitor | 1 mM | $10^6 k_0/s^{-1}$ | 10 mM |
|---|---|---|---|
| None | | 4.0 | |
| Trisodium citrate | 2.7 | | 1.5 |
| Disodium 3,3-dimethylglutarate | 1.1 | | 1.6 |
| Sodium bicarbonate | 1.8 | | 1.3 |
| Sodium fluoride | 1.1 | | 1.2 |
| Sodium bicarbonate | 1.4 | | 1.1 |
| Sodium iodide | 1.2 | | 1.6 |
| Sodium thiocyanate | 2.0 | | 1.5 |
| Disodium adipate | | | 1.3 |
| Disodium succinate | | | 1.6 |
| Disodium maleate | | | 1.4 |

Comparative Test J

The procedure of Test C above was repeated with the modification that disodium 3,3-dimethylglutarate was included at 10 mM as an iminium ion scavenger in all reactions except controls, and that either isoascorbic acid (IAA), or kojic acid (KA) was included (each at 10 mM) as a nitrite ion scavenger. In each case initial concentrations of morpholine and diethanolamine were 5 mM. Results are set out in Table 15 (for samples stored at 22° C.) and Table 16 (for samples stored at 40° C.).

TABLE 15

N-Nitrosamine inhibition in bath gel (Gel 1) at 22° C.; [Morpholine]$_0$ = 5 mM; [Additive]$_0$ = 10 mM; [Disodium dimethylglutarate]$_0$ = 10 mM

| Time (days) | Inhibitor added | pH | [NO$_2$]/ppm NO | [R$_2$NNO]/ppb NO | Inhib/% |
|---|---|---|---|---|---|
| 83 | None (control) | 7 | 7.3 | 510 | |
| 83 | IAA | 7 | 0.9 | 110 | 78 |
| 83 | KA | 7 | 2.9 | 76 | 85 |
| 83 | None (control) | 6 | 2.5 | 200 | |
| 83 | IAA | 6 | 0.34 | 160 | 20 |
| 83 | KA | 6 | 0.7 | 87 | 57 |
| 83 | None (control) | 5 | 0.27 | 340 | |
| 83 | IAA | 5 | 0.12 | 64 | 81 |
| 83 | KA | 5 | 0.21 | 65 | 81 |
| | Additive | | | | |
| 196 | None (control) | 7 | 9.1 | 670 | |
| 196 | IAA | 7 | 0.19 | 77 | 88 |
| 196 | KA | 7 | 2.2 | 130 | 80 |
| 196 | None (control) | 6 | 4.5 | 340 | |
| 196 | IAA | 6 | 0.07 | 60 | 82 |
| 196 | KA | 6 | | | |
| 196 | None (control) | 5 | 0.8 | 280 | |
| 196 | IAA | 5 | 0.15 | 70 | 75 |
| 196 | KA | 5 | 0.2 | 65 | 77 |

TABLE 16

N-Nitrosamine inhibition in bath gel (Gel 1) at 40° C. [Morpholine]$_0$ = [Diethanolamine]$_0$ = 5 mM; [Additive]$_0$ = 10 mM; [Disodium dimethylglutarate]$_0$ = 10 mM

| Time (days) | Additive | pH | [NO$_2$]/ppm NO | [R$_2$NNO]/ppb NO | Inhib/% |
|---|---|---|---|---|---|
| 28 | None (control) | 7 | 12.7 | 900 | |
| 28 | IAA | 7 | 1.3 | 51 | 94 |
| 28 | KA | 7 | 3.1 | 224 | 75 |
| 28 | None (control) | 6 | 10.1 | 860 | |
| 28 | IAA | 6 | 1.8 | 41 | 95 |
| 28 | KA | 6 | 1.9 | 430 | 50 |
| 28 | None (control) | 5 | 2.5 | 400 | |
| 28 | IAA | 5 | 2.3 | 108 | 73 |
| 28 | KA | 5 | 0.2 | 126 | 68 |
| 54 | None (control) | 7 | 12.9 | 2700 | |
| 54 | IAA | 7 | 0.065 | 80 | 97 |
| 54 | KA | 7 | 0.85 | 224 | 92 |
| 54 | None (control) | 6 | 7.7 | 1960 | |
| 54 | IAA | 6 | 0.04 | 36 | 98 |
| 54 | KA | 6 | 0.15 | 410 | 79 |
| 54 | None (control) | 5 | 2.5 | 1050 | |
| 54 | IAA | 5 | 0.02 | 20 | 98 |
| 54 | KA | 5 | 0.02 | 85 | 92 |
| 85 | None (control) | 7 | 7.9 | 2140 | |
| 85 | IAA | 7 | 0.06 | 80 | 96 |
| 85 | KA | 7 | 0.26 | 240 | 89 |
| 85 | None (control) | 6 | 7.2 | 3170 | |
| 85 | IAA | 6 | 0 | 42 | 99 |
| 85 | KA | 6 | 0.15 | 270 | 95 |
| 85 | None (control) | 5 | 2.9 | 2085 | |
| 85 | IAA | 5 | 0 | 21 | 99 |
| 85 | KA | 5 | 0.03 | 85 | 96 |
| 196 | None (control) | 7 | 10.5 | 3370 | |
| 196 | IAA | 7 | 0.02 | 120 | 96 |
| 196 | KA | 7 | 0 | 270 | 92 |
| 196 | None (control) | 6 | 1.7 | 1950 | |
| 196 | IAA | 6 | 0.06 | 36 | 98 |
| 196 | KA | 6 | | | |
| 196 | None (control) | 5 | 1.8 | 5580 | |
| 196 | IAA | 5 | 0.03 | 147 | 97 |
| 196 | KA | 5 | a | a | | a = ampoule broken during storage
NB Control samples do not contain DMG

Comparative Test K

The procedure of Test D above was repeated with the modification that the cream base was as described below (Cream Base 2) and that disodium 3,3-dimethylglutarate was included at 10 mM as an iminium ion scavenger in all reactions except controls and that either isoascorbic acid (IAA), or kojic acid (KA) was included (each at 10 mM) as a nitrite ion scavenger. In each case initial concentrations of morpholine and diethanolamine were 5 mM. Results are set out in Table 17 (for samples stored at 22° C.) and Table 18 (for samples stored at 40° C.).

Cream Base 2

| Component | Concentration (% w/v) |
| --- | --- |
| PEG-5-glyceryl stearate | 5.0 |
| Cetyl alcohol | 1.0 |
| Stearic acid | 2.0 |
| Mineral oil | 8.0 |
| Isopropyl myristate | 3.0 |
| 1,3-Butylene glycol | 2.0 |
| Glycerin | 1.5 |
| Triethanolamine | 0.2 |
| Methyl, butyl and ethyl parabens | 0.4 |
| Water | to 100 |

TABLE 17

N-Nitrosamine inhibition in cream (Cream Base 2) at 22° C.; $[Morpholine]_0 = [Diethanolamine]_0 = 5$ mM; $[Additive]_0 = 10$ mM; $[disodium\ dimethylglutarate]_0 = 10$ mM

| Time (days) | Additive | pH | $[NO_2]/$ ppm NO | $[R_2NNO]$/ppb NO | Inhib/% |
| --- | --- | --- | --- | --- | --- |
| 84 | None (control) | 7 | 8.3 | 1250 | |
| 84 | IAA | 7 | 1.4 | 460 | 63 |
| 84 | KA | 7 | 4.7 | 430 | 66 |
| 84 | None (control) | 6 | 5.7 | 520 | |
| 84 | IAA | 6 | 0.44 | 220 | 58 |
| 84 | KA | 6 | 2.9 | 270 | 48 |
| 84 | None (control) | 5 | 2.5 | 100 | |
| 84 | IAA | 5 | 0.52 | 185 | −85 |
| 84 | KA | 5 | 0.51 | 190 | −90 |
| 196 | None (control) | 7 | 6.4 | 1940 | |
| 196 | IAA | 7 | 1.4 | 490 | 75 |
| 196 | HMT | 7 | | | |
| 196 | KA | 7 | 2.1 | 780 | 60 |
| 196 | None (control) | 6 | 3.5 | 1530 | |
| 196 | IAA | 6 | 0.01 | 68 | 96 |
| 196 | KA | 6 | 0.4 | 560 | 63 |
| 196 | None (control) | 5 | 0.6 | 260 | |
| 196 | IAA | 5 | 0.1 | 100 | 62 |
| 196 | KA | 5 | 0.2 | 83 | 68 |

TABLE 18

N-Nitrosamine inhibition in Cream Base 2 at 40° C.; $[Morpholine]_0 = [Diethanolamine]_0 = 5$ mM; $[Additive]_0 = 10$ mM; $[Disodium\ dimethylglutarate]_0 = 10$ mM

| Time (days) | Additive | pH | $[NO_2]/$ ppm NO | $[R_2NNO]$/ppb NO | Inhib/% |
| --- | --- | --- | --- | --- | --- |
| 21 | None (control) | 7 | 24 | 2080 | |
| 21 | IAA | 7 | 1.7 | 480 | 77 |
| 21 | KA | 7 | 1.5 | 440 | 79 |
| 21 | None (control) | 6 | 7.4 | 1850 | |
| 21 | IAA | 6 | 0.58 | 55 | 97 |
| 21 | KA | 6 | 2.2 | 1060 | 42 |
| 21 | None (control) | 5 | 1.0 | 1020 | |
| 21 | IAA | 5 | 0.2 | 170 | 83 |
| 21 | KA | 5 | 0.3 | 320 | 69 |
| 56 | None (control) | 7 | 7.7 | 4870 | |
| 56 | IAA | 7 | 0.9 | 590 | 88 |
| 56 | KA | 7 | 0.19 | 540 | 89 |
| 56 | None (control) | 6 | 1.5 | 4100 | |
| 56 | IAA | 6 | 0.01 | 56 | 99 |
| 56 | KA | 6 | 0.15 | 1530 | 63 |
| 56 | None (control) | 5 | 0.6 | 1240 | |
| 56 | IAA | 5 | 0.2 | 60 | 95 |
| 56 | KA | 5 | 0.05 | 200 | 84 |
| 88 | None (control) | 7 | 2.7 | 7340 | |
| 88 | IAA | 7 | 1.9 | 720 | 90 |
| 88 | KA | 7 | 0.07 | 450 | 94 |
| 88 | None (control) | 6 | 4.0 | 4260 | |
| 88 | IAA | 6 | 2.4 | 51 | 99 |
| 88 | KA | 6 | 3.7 | 200 | 95 |
| 88 | None (control) | 5 | 0.9 | 1630 | |
| 88 | IAA | 5 | 0 | 63 | 96 |
| 88 | KA | 5 | a | a | |
| 196 | None (control) | 7 | 2.6 | 6670 | |
| 196 | IAA | 7 | 0.3 | 1290 | 80 |
| 196 | KA | 7 | a | a | |
| 196 | None (control) | 6 | 1.0 | 2430 | |
| 196 | IAA | 6 | 0 | 41 | 98 |
| 196 | KA | 6 | 0 | 1750 | 30 |
| 196 | None (control) | 5 | 0.3 | 910 | |
| 196 | IAA | 5 | 0.01 | 39 | 96 |
| 196 | KA | 5 | a | a | | a = ampoule broken during storage
NB Control samples do not contain DMG

EXAMPLE 1

An oil-free skin gel is prepared in conventional manner to the following composition:

| Component | Concentration (% w/v) |
| --- | --- |
| Methyl hydroxybenzoate | 0.1 |
| Propylene glycol | 5 |
| Carbomer 940 | 1 |
| Triethanolamine 99% | 0.6 |
| Disodium EDTA | 0.2 |
| Trisodium citrate | 0.3 |
| Maltol | 0.01 |
| Diazolidinyl urea | 0.3 |
| | water to 100 |

EXAMPLE 2

A self-foaming shaving gel is prepared in conventional manner to the following composition:

| Component | Concentration (% w/v) |
| --- | --- |
| Triethanolamine | 6 |
| Stearic acid | 15 |
| Dimethicone | 1 |
| Polyethylene glycol | 0.25 |
| Sorbitol | 10 |
| Hydroxyethyl cellulose | 0.05 |
| Trisodium citrate | 0.3 |
| Erythorbic acid | 0.01 |

| Component | Concentration (% w/v) |
| --- | --- |
| Isopentane | 2.5 |
| Isobutane | 0.5 |
| | water to 100 |

EXAMPLE 3

A suntan lotion is prepared in conventional manner to the following composition:

| Component | Concentration (% w/v) |
| --- | --- |
| DEA cetyl phosphate | 3 |
| Stearic acid | 4 |
| Cetyl alcohol | 2 |
| Dioctylmaleate | 6 |
| Dimethicone | 0.5 |
| Octyl methoxycinnamate | 3 |
| DEA methoxycinnamate | 3 |
| Carbomer 940 | 0.2 |
| Triethanolamine | 1.2 |
| Glycerin | 10 |
| Propyl paraben | 0.1 |
| Methyl paraben | 0.1 |
| Quaternium - 15 | 0.3 |
| Disodium 3,3-dimethylglutarate | 0.15 |
| Isoascorbic acid | 0.02 |
| | water to 100 |

EXAMPLE 4

A light duty liquid detergent is prepared in conventional manner to the following composition:

| Component | Concentration (% w/v) |
| --- | --- |
| Sodium Alkyl Benzene Sulphonate | 19 |
| Coconut Diethanolamide | 1 |
| Urea | 3 |
| Sodium chloride | 1 |
| Trisodium citrate | 0.3 |
| Maltol | 0.01 |
| Bronopol | 0.02 |
| | water to 100 |

EXAMPLE 5

A facial wash is prepared in conventional manner to the following composition:

| Component | Concentration (% w/v) |
| --- | --- |
| Carbomer 1342 | 1.5 |
| Ethanol | 23 |
| Sodium Laureth Sulphate (28% active) | 3.5 |
| Cocoamidoprapyl betaine | 11.5 |
| Cocamide DEA | 2.3 |
| Triethanolamine | 0.75 |
| Disodium adipate | 0.15 |
| Ethyl maltol | 0.01 |
| Bronopol | 0.02 |
| | water to 100 |

We claim:

1. A method of inhibiting nitrosation reactions in toiletries using an iminium ion scavenger which is an alkali metal adipate and a nitrite ion scavenger which is an ascorbyl phosphate.

2. A method of inhibiting nitrosation reactions in a cosmetics or toiletries composition having water as a carrier material therein, which method comprises employing an iminium ion scavenger which is a member selected from the group consisting of alkali metal glutarates, alkali metal 3,3-dimethylglutarates, alkali metal citrates, alkali metal adipates, alkali metal succinates, and alkali metal maleates, in combination with a nitrite ion scavenger which is an ascorbyl phosphate.

3. The method of claim 2, in which the cosmetics or toiletries composition is in the form of a member selected from the group consisting of cream, gel and lotion.

4. The method of claim 2, in which the iminium ion scavenger is an alkali metal adipate.

5. The method of claim 2, in which the alkali metal is a member selected from the group consisting of sodium and potassium.

6. The method of claim 2, in which the alkali metal adipate is a member selected from the group consisting of sodium adipate and potassium adipate.

7. The method of claim 2, in which the ascorbyl phosphate is magnesium ascorbyl phosphate.

8. The method of claim 2, wherein the iminium ion scavenger is present in a concentration of from about 0.1 mM to about 100 mM in the cosmetics or toiletries composition.

9. The method of claim 2, wherein the nitrite ion scavenger is present in a concentration of from about 0.01 mM to about 50 mM in the cosmetics or toiletries composition.

10. The method of claim 2, wherein the cosmetics or toiletries composition comprises a gem-bromonitro antimicrobial agent.

11. The method of claim 10, wherein the gem-bromonitro antimicrobial agent is bronopol.

12. A method of stabilizing a nitrosatable material so as to inhibit nitrosation reactions, which method comprises adding to the nitrosatable material an effective amount of an iminium ion scavenger in combination with an effective amount of a nitrite ion scavenger.

* * * * *